United States Patent [19]

Borish et al.

[11] Patent Number: 5,354,564
[45] Date of Patent: Oct. 11, 1994

[54] PERSONAL CARE COMPOSITIONS

[75] Inventors: Edward T. Borish; Anne Tashjian, both of Mahwah, N.J.

[73] Assignee: Eastman Kodak Company, Rochester, N.Y.

[21] Appl. No.: 993,132

[22] Filed: Dec. 18, 1992

[51] Int. Cl.⁵ .............................................. A61K 9/16
[52] U.S. Cl. .................................... 424/490; 424/70; 424/401; 424/489; 424/497
[58] Field of Search ................. 424/70, 401, 489, 490, 424/497

[56] References Cited

U.S. PATENT DOCUMENTS

| | | | |
|---|---|---|---|
| 4,145,184 | 3/1979 | Brain et al. | 8/137 |
| 5,145,684 | 9/1992 | Liversidge et al. | 424/489 |
| 5,154,842 | 10/1992 | Walley et al. | 252/8.6 |
| 5,154,847 | 10/1992 | LaPetina et al. | 424/705 |

*Primary Examiner*—Thurman K. Page
*Assistant Examiner*—Jyothsna Venkat
*Attorney, Agent, or Firm*—J. Jeffrey Hawley

[57] ABSTRACT

The present invention is directed to personal care compositions comprising an aqueous dispersion of particles of silicone wherein said particles have a surface modifier adsorbed on the surface thereof in an amount sufficient to achieve a particle size of less than about 400 nanometers (nm). The compositions of the present invention can contain other conventional ingredients.

1 Claim, No Drawings

PERSONAL CARE COMPOSITIONS

FIELD OF THE INVENTION

The present invention relates to personal care compositions and hair care compositions.

BACKGROUND OF THE INVENTION

Silicones have been formulated into compositions that are marketed as personal care and hair care products. However, these agents are poorly soluble in water and require special techniques to achieve stable formulations. Thus, it is an object of the present invention to increase the dispersibility of these agents in aqueous media.

SUMMARY OF THE INVENTION

The present invention is directed to personal care compositions that comprises an aqueous dispersion of particles of silicone wherein said particles have a surface modifier adsorbed on the surface thereof in an amount sufficient to achieve a particle size of less than about 400 nanometers (nm). The compositions of the present invention can contain other conventional ingredients that are used in such compositions.

DETAILED DESCRIPTION OF THE INVENTION

The compositions of the invention comprises nanoparticles containing silicone.

The particles of this invention contain a discrete phase of silicone as described above having a surface modifier adsorbed on the surface thereof. Useful surface modifiers are believed to include those which physically adhere to the surface of at least one of fragrances and thioglycolic acid but do not chemically bond to at least one of fragrances and thioglycolic acid.

Suitable surface modifiers can preferably be selected from known organic and inorganic excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986, the disclosure of which is hereby incorporated by reference in its entirety. The surface modifiers are commercially available and/or can be prepared by techniques known in the art.

The surface modifier is adsorbed on the surface of the silicone in an amount sufficient to maintain an effective average particle size of less than about 400 nm. The surface modifier does not chemically react with the infection control agent or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

The particles of this invention can be prepared by a method comprising the steps of dispersing silicone in a liquid dispersion medium and applying mechanical means in the presence of grinding media to reduce the particle size of the silicone to an effective average particle size of less than about 400 nm. The particles can be reduced in size in the presence of a surface modifier. Alternatively, the particles can be contacted with a surface modifier after attrition.

These methods are described in detail in U.S. Pat. No. 5,145,684.

The relative amount of silicone and surface modifier can vary widely and the optimal amount of the surface modifier can depend, for example, upon the particular silicone and surface modifier selected, the critical micelle concentration of the surface modifier if it forms micelles, etc. The surface modifier preferably is present in an amount of about 0.1–10 mg per square meter surface area of the silicone. The surface modifier can be present in an amount of 0.1–99.995%, preferably 20–60% by weight based on the total weight of the formulation.

The nanoparticles of the present invention can be incorporated into conventional shampoo, detergent or antiperspirant compositions, as for example those disclosed in U.S. Pat. Nos. 4,145,184; 5,154,847; and 5,154,842 the disclosures of which is incorporated herein.

The compositions of the present invention can be illustrated by the following representative example.

| Composition* | Example 1 Concentration Range (%) | Preferred % |
| --- | --- | --- |
| Dimethicone (to be incorporated as nanoparticle) | .1–20 | 1–9 |
| Sodium Laureth Sulfate | 5–30 | 5–15 |
| Cocamide DEA | .1–10 | 1–5 |
| Sodium Chloride | 0–10 | 1–5 |

-continued

Example 1

| Composition* | Concentration Range (%) | Preferred % |
|---|---|---|
| Water | QS | QS |

*Add each ingredient to the water in the order given.

The foregoing specification, including the specific embodiments and example is intended to be illustrative of the present invention and is not to be taken as limiting. Numerous other variations and modifications can be effected without departing from the true spirit and scope of the present invention.

We claim:

1. A personal care composition comprising an aqueous dispersion of particles of dimethicone wherein said particles have a surface modifier adsorbed on the surface thereof in an amount sufficient to achieve a particle size of less than about 400 nanometers (nm), said composition comprising from about 0.1–20 percent by weight dimethicone and the surface modifier is present in an amount of from 1.0–10 mg per square meter surface area of the dimethicone.

* * * * *